United States Patent
Sekimoto et al.

(10) Patent No.: US 7,592,471 B2
(45) Date of Patent: Sep. 22, 2009

(54) TANTALUM COMPOUND, METHOD FOR PRODUCING SAME, TANTALUM-CONTAINING THIN FILM AND METHOD FOR FORMING SAME

(75) Inventors: Kenichi Sekimoto, Tokyo (JP); Ken-ichi Tada, Ayase (JP); Mayumi Takamori, Sagamihara (JP); Tetsu Yamakawa, Ayase (JP); Taishi Furukawa, Ayase (JP); Noriaki Oshima, Yokohama (JP)

(73) Assignees: Tosoh Corporation, Yamaguchi (JP); Sagami Chemical Research Center, Kanagawa (JP)

( * ) Notice: Subject to any disclaimer, the term of this patent is extended or adjusted under 35 U.S.C. 154(b) by 167 days.

(21) Appl. No.: 11/815,386

(22) PCT Filed: Jan. 25, 2006

(86) PCT No.: PCT/JP2006/301116
§ 371 (c)(1),
(2), (4) Date: Aug. 2, 2007

(87) PCT Pub. No.: WO2006/082739
PCT Pub. Date: Aug. 10, 2006

(65) Prior Publication Data
US 2009/0043119 A1    Feb. 12, 2009

(30) Foreign Application Priority Data
Feb. 2, 2005 (JP) .............................. 2005-026727
Feb. 2, 2005 (JP) .............................. 2005-026728
Aug. 24, 2005 (JP) .............................. 2005-243053
Aug. 24, 2005 (JP) .............................. 2005-243054

(51) Int. Cl.
*C07F 17/00* (2006.01)
*H01L 21/4763* (2006.01)
*C23C 16/00* (2006.01)

(52) U.S. Cl. ..................... 556/43; 438/643; 427/255.28
(58) Field of Classification Search ................... 556/43; 438/643; 427/255.28
See application file for complete search history.

(56) References Cited

U.S. PATENT DOCUMENTS 5,130,172 A    7/1992    Hicks et al.
6,491,987 B2    12/2002    Veerasamy et al.
6,743,473 B1    6/2004    Parkhe et al.
2004/0142555 A1*    7/2004    Kamepalli et al. .......... 438/643

FOREIGN PATENT DOCUMENTS

JP    2001-329367 A    11/2001
JP    2002-501075 A    1/2002
WO    2004065650 A2    8/2004

OTHER PUBLICATIONS

A.H. Klazinga et al., 'Synthesis and Properties of Dicyclopentadienyltantalum Hybrice Olefin Compounds', Journal of Organmetallic Chemistry, 1978, vol. 157, pp. 413-419.

Malcolm L.H. Green et al., BIS (n-Isopropylcyclopentadienyl) Tantalum Chemistry: Some Hydride, Carbonyl, Alkyl, Alkyne and Tertiaryphosphine Derivatives, and an Improved Sythesis of Dichlorobiscyclopentadienylniobium, Journal of Organometallic Chemistry, 1980, vol. 193, pp. 339-344.

Xiaomeng Chen et al., "Low temperature plasma-assisted chemical vapor deposition of tantalum nitride from tantalum pentabromide for copper metallization", J. Vac. Sci. Technol., Jan./Feb. 1999, pp. 182-185, vol. 17-1, American Vacuum Society.

Kozoh Sugiyama et al., "Low Temperature Deposition of Metal Nitrides by Thermal Decomposition of Organometallic Compounds", J. Electrochem. Soc., Nov. 1975, pp. 1545-1549, vol. 122, No. 11.

M.H. Tsai et al., "Comparision of the diffusion barrier properties of chemical-vapor-deposited TaN and sputtered TaN between Cu and SI", J. Appl. Phys., May 1, 1996, pp. 6932-6938, vol. 79-9, American Institute of Physics.

M.L.H. Green et al., "The Di-π-cyclopentadienyl Hydrides of Tantalum, Molybdenum, and Tungsten", Journal of The Chemical Society, Nov. 1961, pp. 4854-4859, The Chemical Society, London, Great Britain.

A.H. Klazinga et al., "Synthesis and Properties of Dicyclopentadienyltantalum Hydride Olefin Compounds", Journal of Organometallic Chemistry, 157, 1978, pp. 413-419, Elsevier Sequoia S.A., Lausanne, The Netherlands.

* cited by examiner

*Primary Examiner*—Porfirio Nazario Gonzalez
(74) *Attorney, Agent, or Firm*—Sughrue Mion, PLLC

(57) ABSTRACT

A novel tantalum compound, a method for producing the novel tantalum compound, and a method for stably forming a tantalum-containing thin film which contains the desired element. The tantalum compound enables one to selectively form a tantalum-containing thin film free of halogen and the like, and various tantalum-containing thin films which contain the desired element.

9 Claims, 6 Drawing Sheets

[Fig. 1]
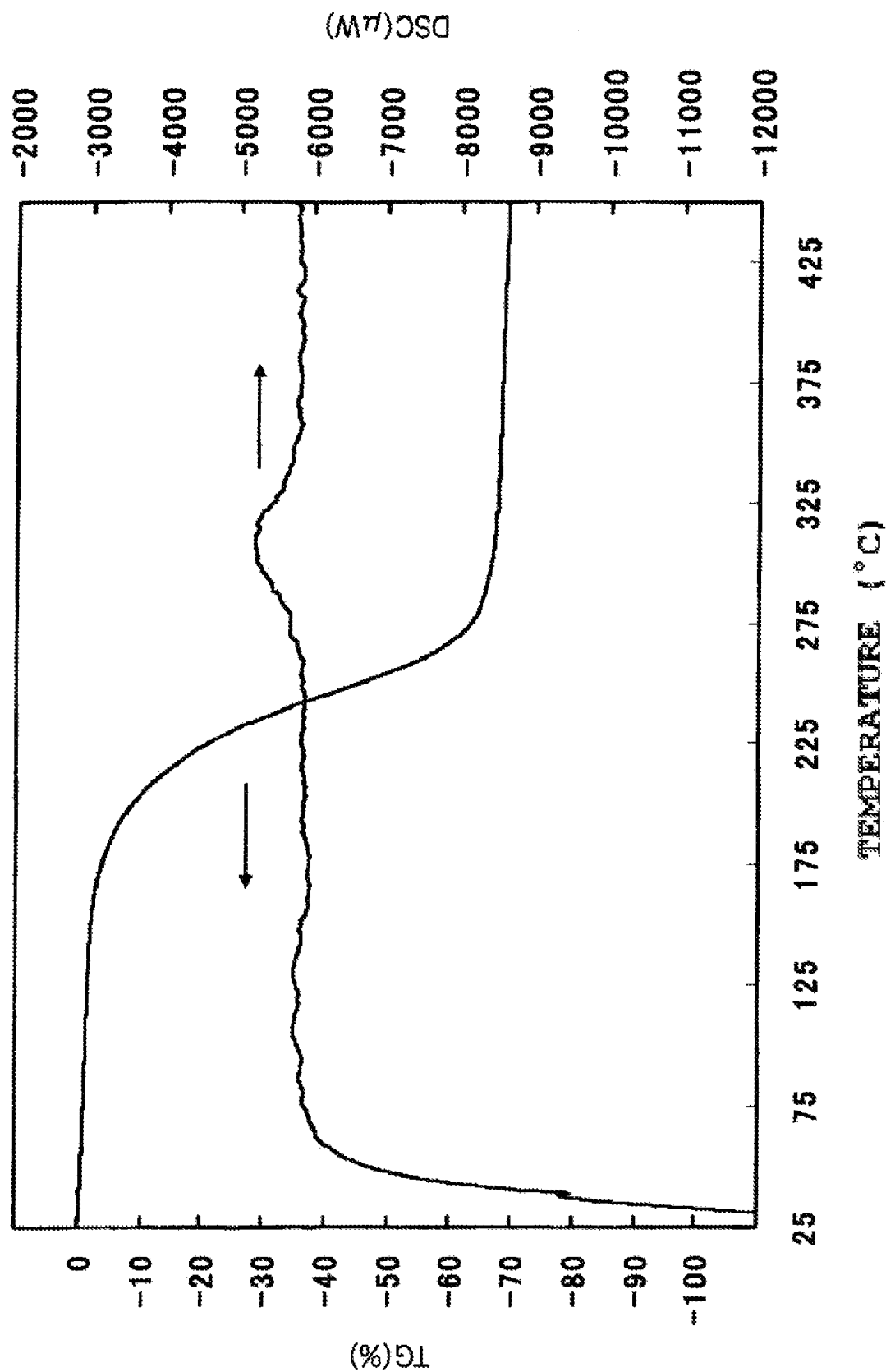

[Fig. 2]
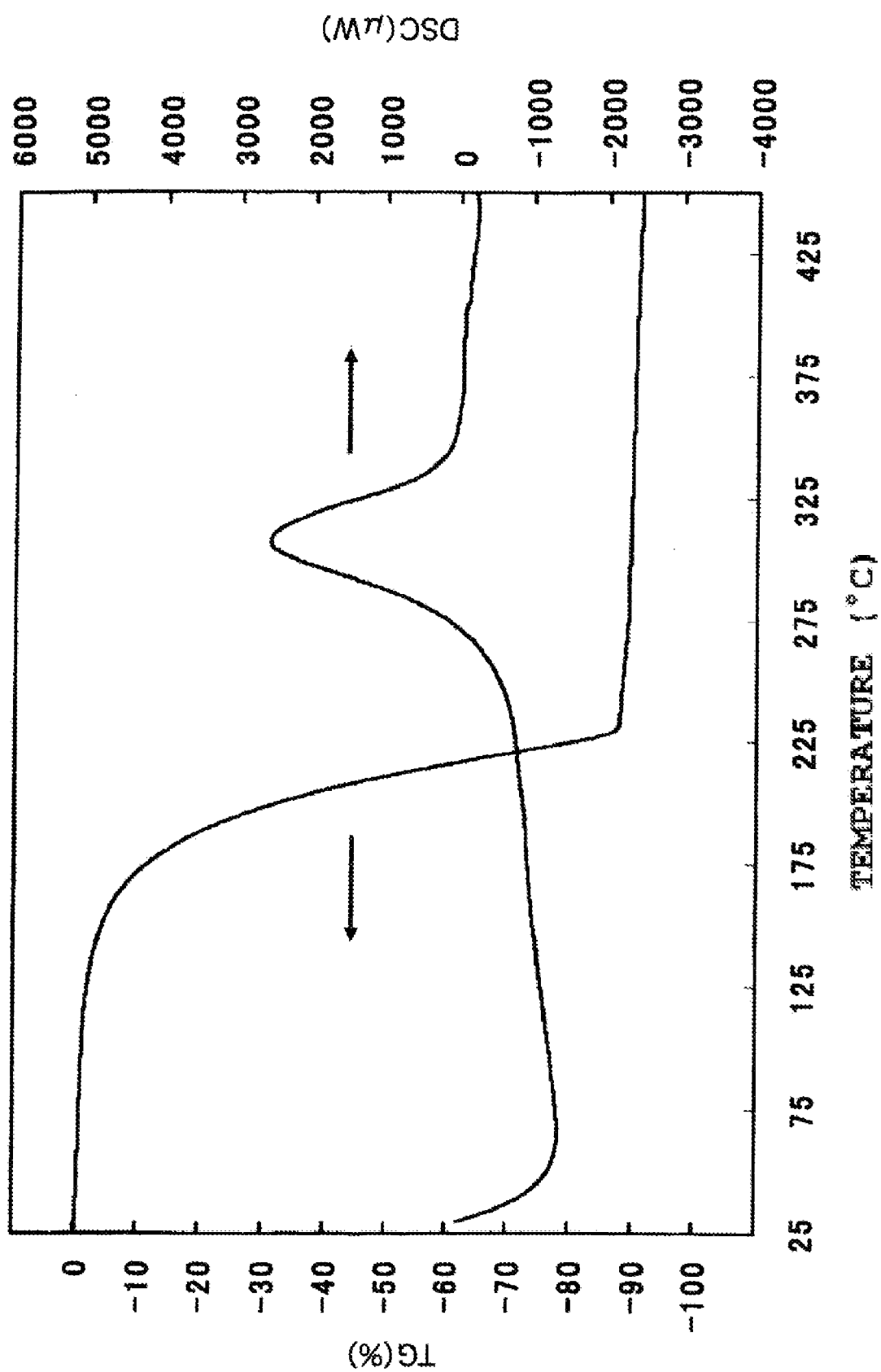

[Fig. 3]
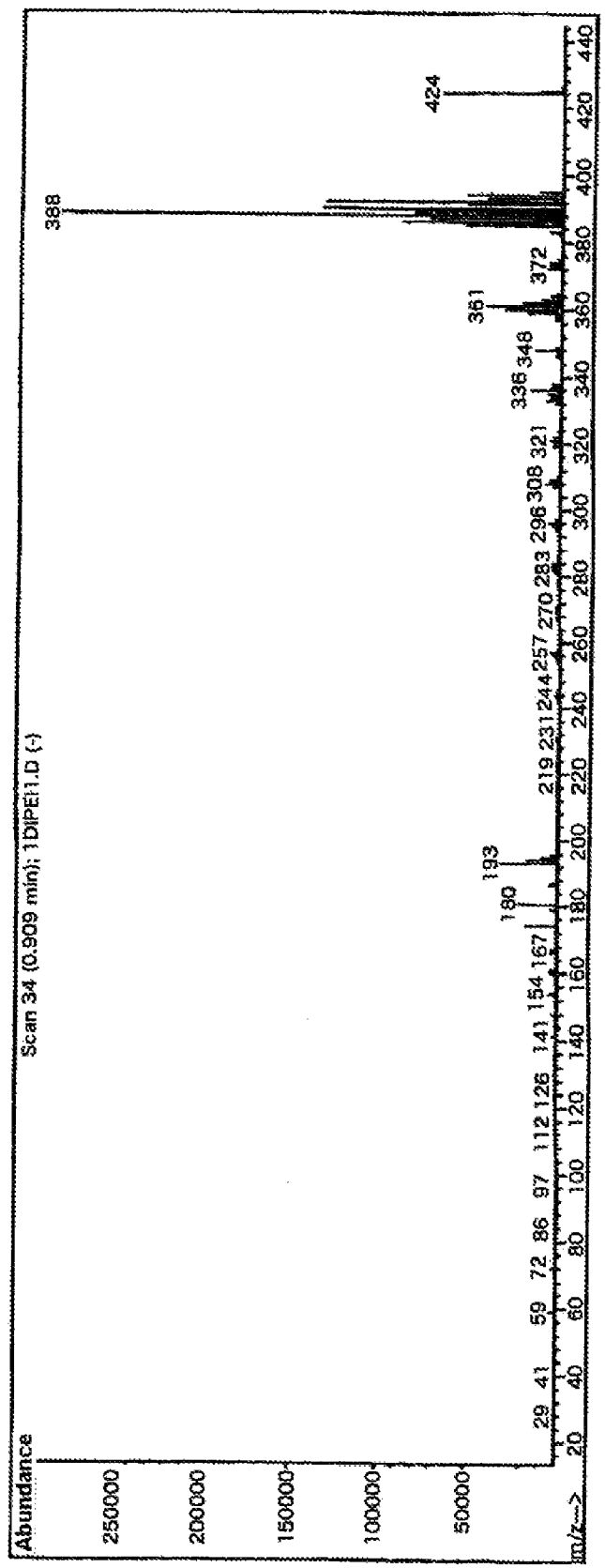

[Fig. 4]
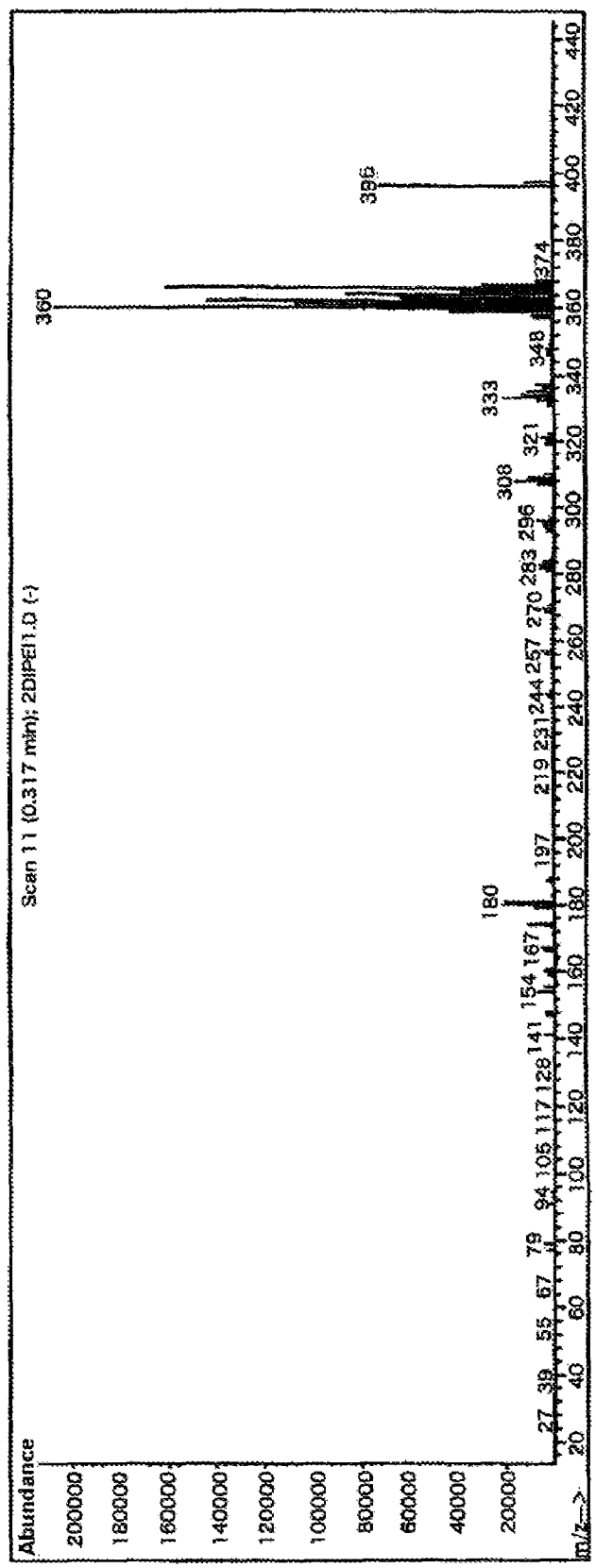

[Fig. 5]
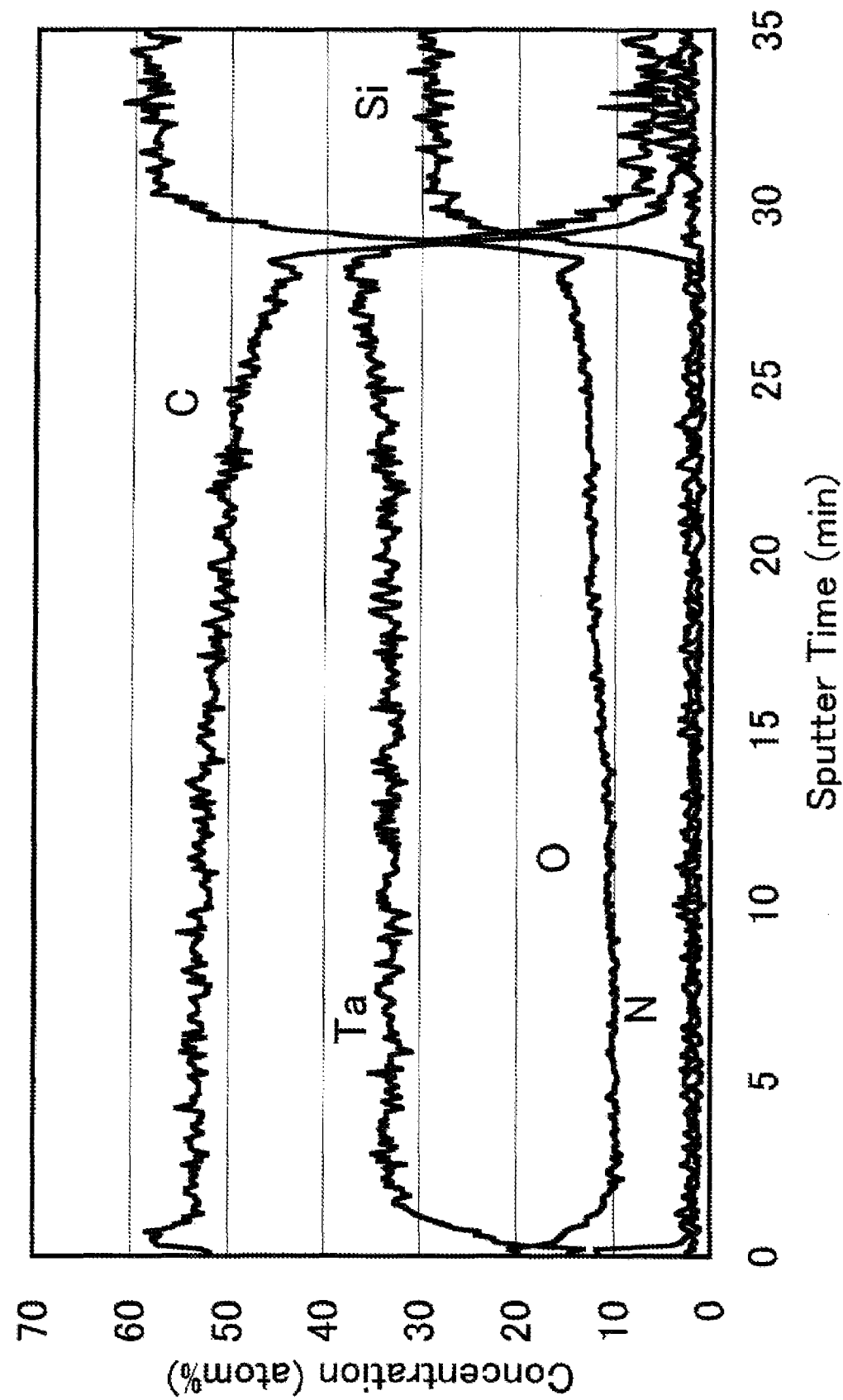

[Fig. 6]
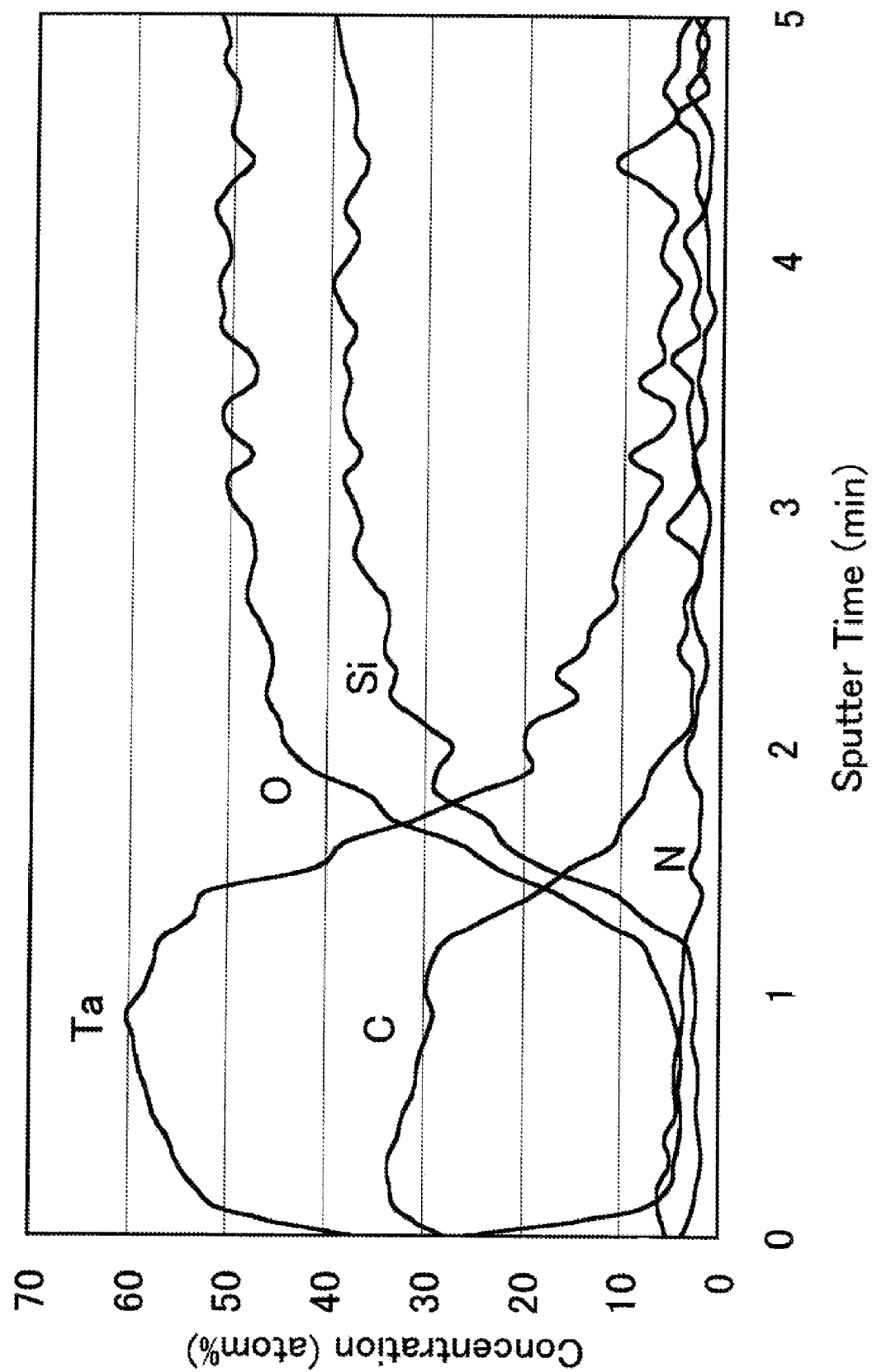

TANTALUM COMPOUND, METHOD FOR PRODUCING SAME, TANTALUM-CONTAINING THIN FILM AND METHOD FOR FORMING SAME

TECHNICAL FIELD

The present invention relates to a novel tantalum compound and a method for producing the same. The tantalum compound of the present invention is useful for the formation of a tantalum-containing thin film by a chemical vapor deposition method (CVD method) or an atomic layer deposition method (ALD method). Further, it relates to a method for forming a tantalum-containing thin film which is useful for the production of semiconductor devices, and a tantalum-containing thin film.

BACKGROUND ART

Miniaturization of device structure is advanced with enhanced performance of semiconductor devices. Width of wiring in a device becomes fine, and aluminum conventionally used as a wiring material gives rise a problem in delay of signal transmission. As a result, copper has been used. Copper has the characteristic that resistance is low, but has the disadvantage that it is liable to be diffused in a silicon oxide used in an insulating film between wirings, resulting in degradation of performance of the insulating film. For this reason, a method is employed that a barrier film for preventing the diffusion is provided between the wiring and the insulating film. As the barrier film, a tantalum nitride film is generally used from high ability of preventing diffusion of copper. However, the tantalum nitride film has poor adhesion to a copper seed film for forming a copper wiring by plating, and film peeling occurs between the tantalum nitride film and the copper seed film when forming a wiring or planarizing after wiring formation, resulting in generation of defect. For this reason, a method is employed that a metallic tantalum film is formed between the tantalum nitride film as a barrier film and the copper seed film, thereby preventing the film peeling.

At present, a tantalum nitride film and a metallic tantalum film are mainly formed by a physical vapor deposition method (PVD method) by sputtering. In the PVD method, it is difficult to form a uniform film on a concave-convex surface, and from now, where miniaturization of a semiconductor device is advanced, it will be required to form a uniform and thin film on a surface of a complicated three dimensional structure. Because of this, investigation is made in formation by a chemical vapor deposition method (CVD method) that decomposes raw material gases of a metal halide, an amide compound, an organic metal compound and the like to deposit a film, or by an atomic layer deposition method (ALD method) that decomposes those raw materials adsorbed on a substrate surface to deposit a film.

When a tantalum nitride film or a metallic tantalum film is formed by CVD method or ALD method, it is desirable that both films can be formed from the same tantalum raw material in one reaction chamber. As a raw material of such a formation method, a halide such as $TaCl_5$ and $TaBr_5$ is investigated (for example, see Non-Patent Document 1). Further, as a raw material of a tantalum nitride film, an amide compound such as $Ta(NMe_2)_5$, $Ta(NEt_2)_5$ (for example, see Non-Patent Document 2) and $^tBuN=Ta(NEt_2)_3$ (for example, see Non-Patent Document 3) is investigated. However, the halide has high melting point and is required to vaporize by sublimation. Thus, it is difficult to use the halide as a raw material in CVD method or ALD method. Additionally, there are the problems on corrosion of a film due to a residual halogen in a film, deterioration of adhesion and the like. On the other hand, in the amide compound, because nitrogen remains in a film, it is possible to form a tantalum nitride film, but it is difficult to form a metallic tantalum film. For this reason, a tantalum raw material for CVD or ALD that does not contain a halogen and nitrogen in the molecule is required, and a method of using an organometallic compound such as $((Si(CH_3)_3)C_5H_4)Ta(CO)_4$ (see Patent Document 1) or $((Si(CH_3)_3)C_5H_4)_2TaH_3$ (see Patent Document 2) is investigated. However, there are the problems that those tantalum compounds have low heat stability, and are difficult to vaporize stably.

$Cp_2TaH_3$ (see Non-Patent Document 4) and $Cp_2Ta(CO)H$ (see Non-Patent Document 5) are known a tantalum-containing organometallic compound.

Patent Document 1: U.S. Pat. No. 6,491,987
Patent Document 2: U.S. Pat. No. 6,743,473
Non-Patent Document 1: X. Chen, H. L. Frisch, A. E. Kaloyeros, B. Arkles and J. Sullivan, J. Vac. Sci. Technol. B 1999, 17, 182
Non-Patent Document 2: K. Sugiyama, S. Pac, Y. Takahashi and S. Motojima, J. Electrochem. Soc. 1975, 122, 1545
Non-Patent Document 3: M. H. Tsai, S. C. Sun, C. E. Tsai, S. H. Chuang and H. T. Chiu, J. Appl. Phys. 1996, 79, 6932
Non-Patent Document 4: M. L. H. Green, J. A. McCleverty, L. Pratt and G. Wilkinson, J. Chem. Soc. 1961, 4854
Non-Patent Document 5: A. H. Klazing and J. H. Teuben, J. Organomet. Chem. 1978, 157, 413

DISCLOSURE OF THE INVENTION

Problems that the Invention is to Solve

A first object of the present invention is to provide a novel tantalum compound which does not contain a halogen and nitrogen in its molecule, and enables to selectively form a tantalum-containing thin film which does not contain those elements, and various tantalum-containing thin films containing the desired element by the addition of a reactive gas, and a method for producing the same. Further, a second object of the present invention is to provide a method for stably forming a tantalum-containing thin film which contains the desired element, and a tantalum-containing thin film which contains an optional element.

Means for Solving the Problems

As a result of keen investigations, the present inventors have found that the above first object can be achieved by tantalum compounds represented by the following general formulae (1) and (2).

That is, the first invention is a tantalum compound characterized in that it is represented by the following general formula (1)

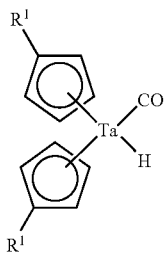

(1)

[Chem. 1]

(In the formula, $R^1$ represents a straight-chain alkyl group having from 2 to 6 carbon atoms).

Further, it is a tantalum compound characterized in that it is represented by the following general formula (2)

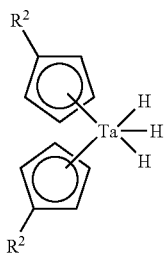

(2)

[Chem. 2]

(In the formula, $R^2$ represents a straight-chain alkyl group having from 2 to 6 carbon atoms).

Further, it is a method for producing the tantalum compound represented by the general formula (2), which is characterized by reacting a tantalum halide represented by the following general formula (3)

[Chem. 3]

$$TaX_5 \quad (3)$$

(In the formula, X represents a halogen), an alkali metal salt of a substituted cyclopentadiene represented by the following general formula (4)

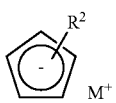

(4)

[Chem. 4]

(In the formula, $R^2$ represents a straight-chain alkyl group having from 2 to 6 carbon atoms, and M represents an alkali metal), and a reducing agent.

Further, it is a method for producing the tantalum compound represented by the general formula (1), which is characterized by reacting carbon monoxide with the tantalum compound represented by the general formula (2).

Further, the present inventors have found that the above second object can be achieved by using a tantalum compound represented by the following general formula (6) as a raw material.

That is, the second invention is a method for forming a tantalum-containing thin film, which is characterized by using a tantalum compound represented by the following general formula (6)

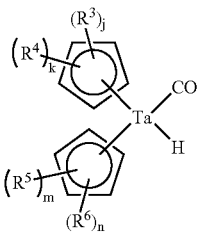

(6)

[Chem. 5]

(In the formula, j, k, m and n are an integer of from 1 to 4 satisfying j+k=5 and m+n=5, and $R^3$ to $R^6$ represent a hydrogen atom, an alkyl group having from 1 to 6 carbon atoms, a trialkylsilyl group having from 3 to 6 carbon atoms or an alkyl group having from 1 to 6 carbon atoms which may be substituted with at least one fluorine atom) as a raw material. Further, it is a tantalum-containing thin film formed by the method.

ADVANTAGE OF THE INVENTION

A novel tantalum compound of the present invention can be used as a raw material of a tantalum-containing thin film by CVD method or ALD method from its vaporization and decomposition characteristics. Further, because of not containing a halogen and nitrogen in its molecule, it is possible to form a tantalum-containing thin film which does not contain those elements, and to form various tantalum-containing thin films which contain the desired element by the addition of a reactive gas. Further, a novel tantalum compound of the present invention can expect a function as a reaction catalyst.

Further, the method for forming a tantalum-containing thin film of the present invention makes it possible to stably form various tantalum thin films containing the desired element, such as a metallic tantalum thin film and a tantalum nitride thin film.

BRIEF DESCRIPTION OF THE DRAWINGS

FIG. 1 shows the result of thermal analysis (TG and DSC) of the tantalum compound obtained in Example 2.

FIG. 2 shows the result of thermal analysis (TG and DSC) of the tantalum compound obtained in Example 5.

FIG. 3 shows the result of mass spectrum measurement of the tantalum compound obtained in Example 2.

FIG. 4 shows the result of mass spectrum measurement of the tantalum compound obtained in Example 5.

FIG. 5 shows a distribution state of elements in a depth direction of the tantalum-containing thin film obtained in Example 8.

FIG. 6 shows a distribution state of elements in a depth direction of the tantalum-containing thin film obtained in Example 9.

BEST MODE FOR CARRYING OUT THE INVENTION

The present invention is described in further detail below. In the description, Cp means a cyclopentadienyl group, Et means an ethyl group, Pr means a propyl group, Bu means a butyl group and THF means tetrahydrofuran.

First, the first invention is described in detail. In the above general formulae (1) and (2), $R^1$ and $R^2$ represent a straight-chain alkyl group having from 2 to 6 carbon atoms. When used as a raw material of a tantalum-containing thin film by CVD method or ALD method, it is desirable that vapor pressure is high, it is liquid at room temperature and at least a melting point is 40° C. or lower. From this point, $R^1$ and $R^2$ are preferably a straight-chain alkyl group having from 2 to 4 carbon atoms, more preferably an ethyl group (C=2) or a propyl group (C=3), and most preferably an ethyl group.

The tantalum compound represented by the above general formula (2) can be synthesized by using a tantalum halide such as $TaCl_5$ shown by the general formula (3) as a raw material. The synthesis method can apply a method known as the synthesis method of $TaCp_2H_3$. For example, the following method can be applied; a method of reacting the tantalum halide represented by the above general formula (3) and isopropyl magnesium bromide, reacting an alkali metal salt of the substituted cyclopentadiene represented by the general formula (4) to synthesize a tantalum compound represented by the general formula (5)

[Chem. 6]

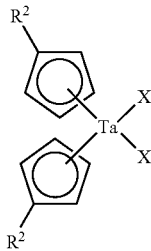

(5)

(In the formula, $R^2$ represents a straight-chain alkyl group having from 2 to 6 carbon atoms, and X represents a halogen), and reacting a reducing agent with this compound to synthesize, as described in M. L. H. Green and B. Jousseaume, J. Organomet. Chem. 1980, 193, 339, or a method of adding the tantalum halide represented by the above general formula (3) to an alkali metal salt of the substituted cyclopentadiene represented by the above general formula (4) and a reducing agent, and heating, as described in M. L. H. Green, J. A. McCleverty, L. Pratt and G. Wilkinson, J. Chem. Soc. 1961, 4854.

In those reactions, as the tantalum halide, $TaCl_5$, $TaBr_5$, $TaI_5$ and the like can be used, and $TaCl_5$ is preferable in the points of cost and availability. As the reducing agent, $NaAlH_2(OCH_2CH_2OCH_3)_2$, $NaBH_4$, $LiAlH_4$ and the like can be used. The alkali metal salt of the substituted cyclopentadiene is preferably Na salts, K salts and Li salts. As the reaction solvent, ether solvents such as diethyl ether and THF, and hydrocarbon solvents such as hexane, heptane, octane, toluene and xylene can be used.

The tantalum compound represented by the above general formula (1) can be synthesized by reacting carbon monoxide with the tantalum compound represented by the general formula (2). The reaction can be conducted in a carbon monoxide atmosphere under pressure or at normal pressures by dissolving or suspending the tantalum compound represented by the general formula (2) in a solvent. When the reaction is conducted at normal pressures, it is preferable to conduct the reaction at a temperature of 100° C. or higher from the point that reaction time can be shortened. In this case, a solvent used is preferably a hydrocarbon solvent having a boiling point of 100° C. or higher, such as toluene, xylene, octane, nonane and decane. The substituent $R^2$ in the tantalum compound represented by the general formula (2) directly constitutes the substituent $R^1$ in the tantalum compound represented by the general formula (1) without receiving change by this reaction.

The tantalum compound represented by the above general formula (1) and the tantalum compound represented by the general formula (2) can be vaporized at 200° C. or lower from thermal analysis (TG and DSC) and thermally decompose at 200 to 300° C. Therefore, those compounds can be used as a raw material for the formation of a tantalum-containing thin film by CVD method or ALD method.

Next, the second invention is described in detail.

In the above formula, a methyl group, an ethyl group, a propyl group, a butyl group, a pentyl group, a hexyl group, an isopropyl group, a tert-butyl group and the like can be exemplified as the alkyl group having from 1 to 6 carbon atoms, and a trimethylsilyl group, an ethyldimethylsilyl group, a diethylmethylsilyl group, a triethylsilyl group and the like can be exemplified as the trialkylsilyl group having from 3 to 6 carbon atoms shown by $R^3$, $R^4$, $R^5$ and $R^6$. Further, a trifluoromethyl group, a perfluoroethyl group, a perfluoropropyl group, a perfluorobutyl group, a perfluoropentyl group, a perfluorohexyl group, a perfluoroisopropyl group, a perfluoro-tert-butyl group and the like can be exemplified as the alkyl group having from 1 to 6 carbon atoms which may be substituted with at least one fluorine atom.

The second invention is characterized in that the tantalum compound of the above general formula (6) is used as a raw material of a tantalum-containing thin film, but a method for forming the tantalum-containing thin film from the tantalum compound of the above general formula (6) is not particularly limited. To form a uniform film on a convex-concave surface, CVD method or ALD method is preferable as a film-forming method. In CVD method or ALD method, a raw material preferably has low melting point and high vapor pressure. When a raw material is used alone, it is preferable in the above general formula (6) that j=1, m=1, $R^4$ and $R^6$ are a hydrogen atom, and $R^3$ and $R^5$ are a straight-chain alkyl group having from 1 to 4 carbon atoms, a trimethylsilyl group or a trifluoromethyl group, and is more preferable that $R^4$ and $R^6$ are a hydrogen atom, and $R^3$ and $R^5$ are a straight-chain alkyl group having from 2 to 4 carbon atoms. It is preferable that $R^4$ and $R^6$ are a hydrogen atom, and $R^3$ and $R^5$ are an ethyl group or a propyl group, and it is particularly preferable that $R^4$ and $R^6$ are a hydrogen atom, and $R^3$ and $R^5$ are an ethyl group.

The tantalum compound represented by the above general formula (6) can be synthesized by reacting carbon monoxide with $Ta((R^3)_j(R^4)_kCp)((R^5)_m(R^6)_nCp)H_3$ that can be synthesized from a tantalum halide such as $TaCl_5$.

The synthesis method of $Ta((R^3)_j(R^4)_kCp)((R^5)_m(R^6)_nCp)H_3$ can apply a method known as the synthesis method of $TaCp_2H_3$ when $(R^3)_j(R^4)_kCp$ and $(R^5)_m(R^6)_nCp$ are the same. For example, the following method can be applied; a synthesis method by reacting a tantalum halide and isopropyl magnesium bromide, reacting an alkali metal salt of a substituted cyclopentadiene to synthesize $Ta((R^3)_j(R^4)_kCp)((R^5)_m(R^6)_nCp)X_2$ (X represents a halogen), and reacting a reducing agent with this, as described in M. L. H. Green and B. Jousseaume, J. Organomet. Chem. 1980, 193, 339, or a method of adding a tantalum halide to an alkali metal salt of a substituted cyclopentadiene and a reducing agent, and heating, as described in M. L. H. Green, J. A. McCleverty, L. Pratt and G. Wilkinson, J. Chem. Soc. 1961, 4854. When $(R^3)_j(R^4)_k$Cp and $(R^5)_m(R^6)_n$Cp are different, for example, it can be synthesized from $Ta((R^3)_j(R^4)_k Cp)((R^5)_m(R^6)_n Cp)X_2$ synthesized by introducing $(R^3)_j(R^4)_k$Cp and $(R^5)_m(R^6)_n$Cp one by one as described in V. C. Gibson, J. E. Bercaw, W. J. Bruton, Jr. and R. D. Sanner Organometallics 1986, 5, 976.

In those reactions, as the tantalum halide, $TaCl_5$, $TaBr_5$, $TaI_5$ and the like can be used, and $TaCl_5$ is preferable from the points of cost and availability. As the reducing agent, $NaAlH_2(OCH_2CH_2OCH_3)_2$, $NaBH_4$, $LiAlH_4$ and the like can be used. Further, the alkali metal salt of the substituted cyclopentadiene is preferably Na salts, K salts and Li salts. As the reaction solvent, ether solvents such as diethyl ether and THF, and hydrocarbon solvents such as hexane, heptane, octane, toluene and xylene can be used.

The reaction of $Ta((R^3)_j(R^4)_k Cp)((R^5)_m(R^6)_n Cp)H_3$ and carbon monoxide can be conducted in a state of dissolving or dispersing in a solvent under pressure or at normal pressures in a carbon monoxide atmosphere. When the reaction is conducted at normal pressures, it is preferable to conduct the reaction at a temperature of 100° C. or higher from the point that reaction time can be shortened. In this case, a solvent used is preferably a hydrocarbon solvent having a boiling point of 100° C. or higher, such as toluene, xylene, octane, nonane and decane.

In forming a tantalum-containing thin film, it is possible to use the tantalum compound represented by the general formula (6) as a raw material and dissolve the same in an organic solvent. The organic solvent used in this case is not particularly limited so far as it does not react with the tantalum compound, and hydrocarbon solvents such as hexane, cyclohexane, heptane, octane, toluene and xylene are preferably used.

When CVD method or ALD method is used, a raw material is gasified and supplied onto a substrate, and its method can be carried out by a bubbling method of blowing a carrier gas such as Ar into a liquefied raw material and supplying the raw material gas together with the carrier gas onto a substrate; a sublimation method of heating a solid raw material to sublimate and supplying the raw material gas together with a carrier gas onto a substrate; a liquid injection method of vaporizing a liquefied raw material or a solution of a raw material in a vaporizer and supplying the gas onto a substrate; and the like.

Formation of a thin film is carried out by decomposing a raw material supplied onto a substrate. It is possible to conduct the decomposition with only heat, but plasma, light and the like may be used together. In forming the thin film, it is possible to change the composition of the thin film by coexisting a reactive gas. It is possible to form a metallic tantalum thin film by supplying a reducing gas such as hydrogen, followed by film formation, and it is possible to form a tantalum nitride thin film by supplying a N-containing gas such as ammonia, methylhydrazine, dimethylhydrazine, ethylhydrazine, diethylhydrazine, butylhydrazine, phenylhydrazine, ethyl azide, butyl azide or phenyl azide, followed by film formation. Besides, it is possible to form a tantalum silicide thin film by supplying a Si-containing gas such as monosilane, disilane, dichlorosilane, trichlorosilane or tetrachlorosilane, followed by film formation, and it is possible to form a tantalum oxide thin film by supplying an oxygen-containing gas such as oxygen, ozone or water vapor, followed by film formation. It is further possible to form a tantalum carbide thin film, a tantalum carbonitride thin film and a tantalum siliconitride thin film, depending on the combination of reactive gases, film formation conditions and the like.

Film-forming methods other than CVD method and ALD method, for example, film-forming methods by a spin coating method, a dipping method, a spraying method and the like that supply a raw material in a form of a liquid or a solution, are included in the present invention.

Specific embodiments applying the present invention are described in detail below by referring to the Examples, but it should be understood that the invention is not construed as being limited thereto.

EXAMPLE 1

Synthesis of trihydridobis(propylcyclopentadienyl) tantalum $(Ta(PrCp)_2H_3)$ 80.0 g (223 mmol) of tantalum pentachloride was suspended in 1,340 ml of ether, and 324 ml (220 mmol) of isopropyl magnesium bromide (0.68M THF solution) was added thereto. A solution of 50.2 g (440 mmol) of propylcyclopentadienyl lithium prepared from propylcyclopentadiene and butyl lithium in THF (380 ml) was added, followed by refluxing for 1 hour. The solvent was distilled away, and the residue was dried at 80° C. in vacuo for 8 hours to obtain a brownish-red solid containing dichlorobis(propylcyclopentadienyl)tantalum $(Ta (PrCp)_2Cl_2)$. 2,100 ml of toluene was added to this brownish-red solid, and the resulting mixture was ice-cooled. 198 ml (660 mmol) of a toluene solution (65 wt %) of sodium bis(2-methoxyethoxy)aluminum hydride was added dropwise to the mixture, and temperature was returned to room temperature, followed by stirring for 19.5 hours. 106 ml of water was added to the mixture, followed by stirring until foaming does not occur. Insoluble contents were filtered out, and the solvent was distilled away from the filtrate. 2,000 ml of hexane was added to the residue, the insoluble contents were filtered out, and the filtrate was concentrated to about 800 ml. When the concentrated liquid was cooled to −70° C., a white solid was formed. A supernatant was removed, and the solid was washed with 40 ml of cold pentane two times to obtain 11.2 g (yield: 12.8%) of a white solid.

$^1$H-NMR (Benzene-$d_6$, δ ppm) 4.84 (m, 4H, $C_5\underline{H}_4$Pr) 4.74 (dd, J=2.5 Hz, 4H, $C_5\underline{H}_4$Pr) 2.34 (t, J=7.8 Hz, 4H, $CH_3CH_2C\underline{H}_2$ Cp) 1.44 (tq, J=7.5 Hz, 4H, $CH_3C\underline{H}_2CH_2$ Cp) 0.82 (t, J=7.5 Hz, 6H, $C\underline{H}_3CH_2CH_2$ Cp) −0.84 (t, J=10.8 Hz, 2H, Ta—$\underline{H}$) −2.35 (d, J=10 Hz, 1H, Ta—$\underline{H}$)

$^{13}$C-NMR (Benzene-$d_6$, δ ppm) 112.58 ($\underline{C}_5H_4$Pr) 86.63 ($\underline{C}_5H_4$Pr) 84.61 ($\underline{C}_5H_4$Pr) 33.21 ($CH_3CH_2\underline{C}H_2$ Cp) 25.83 ($CH_3\underline{C}H_2CH_2$ Cp) 14.11 ($\underline{C}H_3CH_2CH_2$Cp)

EXAMPLE 2

Synthesis of hydridobis(propylcyclopentadienyl) carbonyl-tantalum $(Ta(PrCp)_2(CO)H)$ 11.2 g (28.1 mmol) of trihydridobis(propyl-cyclopentadienyl)tantalum was heated to 135° C. in nonane (200 ml) under a carbon monoxide atmosphere, and stirred for 4 hours. The solvent was distilled away from the reaction mixture, and a solution hexane-extracted from the residue was concentrated to about 200 ml, and then cooled to −70° C. The supernatant was removed, and the solid was washed with 20 ml of hexane two times, and dried in vacuo to obtain 7.45 g (yield: 62.4%)

of a purple solid. Thermal analysis result of the tantalum compound obtained is shown in FIG. 1. It is seen from this Figure that the tantalum compound obtained has a wide temperature range at which the compound can vaporize stably without decomposition, and thermally decomposes in the vicinity of 260° C., and the compound is therefore suitable as a raw material of a tantalum-containing thin film by CVD method or ALD method.

$^1$H-NMR (Benzene-d$_6$, δ ppm) 4.52 (m, 4H, C$_5$H$_4$Pr) 4.46 (m, 2H, C$_5$H$_4$Pr) 4.41 (m, 2H, C$_5$H$_4$Pr) 2.20 (t, J=7.8 Hz, 4H, CH$_3$CH$_2$CH$_2$ Cp) 1.40 (m, 4H, CH$_3$CH$_2$CH$_2$ Cp) 0.83 (t, J=7.5 Hz, 6H, CH$_3$CH$_2$CH$_2$ Cp) −6.09 (s, 1H, Ta—H)

$^{13}$C-NMR (Benzene-d$_6$, δ ppm) 264.63 (CO) 109.89 (C$_5$H$_4$Pr) 84.58 (C$_5$H$_4$Pr) 84.37 (C$_5$H$_4$Pr) 82.13 (C$_5$H$_4$Pr) 80.03 (C$_5$H$_4$Pr) 32.60 (CH$_3$CH$_2$CH$_2$ Cp) 25.79 (CH$_3$CH$_2$CH$_2$ Cp) 14.12 (CH$_3$CH$_2$CH$_2$ Cp)

IR (Nujol, ν cm$^{-1}$) 1896 (CO) 1721 (Ta—H)

Compositional Analysis

Ta content (ICP emission analysis)
    42.7 wt % (theoretical value 42.6 wt %)

CH content (Elemental analysis)
    C 46.7 wt % (theoretical value 48.1 wt %)
    H 5.3 wt % (theoretical value 5.5 wt %)

MS (GC/MS, EI)
    Molecular ion peak of hydridobis(propylcyclopenta-dienyl)carbonyltantalum by $^{181}$Ta, m/z: 424
    Chart of this mass spectrum is shown in FIG. 3.

EXAMPLE 3

Synthesis (1) of bis(ethylcyclopentadienyl)trihydrido-tantalum (Ta(EtCp)$_2$H$_3$)

75.0 g (209 mmol) of tantalum pentachloride was suspended in 1,200 ml of ether, and 335 ml (228 mmol) of isopropyl magnesium bromide (0.68M THF solution) was added thereto. A solution of 41.9 g (419 mmol) of ethylcylopentadienyl lithium prepared from ethylcyclopentadiene and butyl lithium in THF (240 ml) was added, followed by refluxing for 1 hour. The solvent was distilled away, and the residue was dried at 80° C. in vacuo for 8 hours to obtain a dark brown solid containing bis(ethylcyclopentadienyl)dichlorotantalum (Ta(EtCp)$_2$Cl$_2$). 1,060 ml of toluene was added to this dark brown solid, and the resulting mixture was ice-cooled. 187 ml (623 mmol) of a toluene solution (65 wt %) of sodium bis(2-methoxyethoxy)aluminum hydride was added dropwise to the mixture, and temperature was returned to room temperature, followed by stirring for 17 hours. 107 ml of water was added to the mixture, followed by stirring until foaming does not occur. Insoluble contents were filtered out, and the solvent was distilled away from the filtrate. 590 ml of hexane was added to the residue, the insoluble contents were filtered out. When the filtrate was cooled to −70° C., a white solid was formed. The supernatant was removed, and the solid was washed with 24 ml of cold pentane two times to obtain a solid. The solid obtained was distilled in vacuo at 2.5 Pa/100° C. to obtain 7.79 g (yield: 10.1%) of a colorless liquid. When this liquid was cooled to room temperature, white crystals were formed.

$^1$H-NMR (Benzene-d$_6$, δ ppm) 4.79 (m, 4H, C$_5$H$_4$Et) 4.72 (t, J=2.5 Hz, 4H, C$_5$H$_4$Et) 2.38 (q, J=7.5 Hz, 4H, CH$_3$CH$_2$Cp) 1.06 (t, J=7.5 Hz, 6H, CH$_3$CH$_2$Cp) −0.88 (t, J=10.5 Hz, 1H, Ta—H) −2.42 (d, J=10.5 Hz, 2H, Ta—H)

$^{13}$C-NMR (Benzene-d$_6$, δ ppm) 114.91 (C$_5$H$_4$Et) 85.64 (C$_5$H$_4$Et) 84.44 (C$_5$H$_4$Et) 23.78 (CH$_3$CH$_2$ Cp) 15.98 (CH$_3$CH$_2$ Cp)

EXAMPLE 4

Synthesis (2) of bis(ethylcyclopentadienyl)trihydrido-tantalum (Ta(EtCp)$_2$H$_3$)

6.85 g (181 mmol) of sodium borohydride and 40 ml of THF were added to a solution of 48.9 g (489 mmol) of ethylcyclopentadienyl lithium prepared from ethylcyclopentadiene and butyl lithium in THF (200 ml), followed by ice-cooling. 24.9 g (69 mmol) of tantalum pentachloride was added to the mixture, followed by refluxing for 4 hours. The solvent was distilled away in vacuo, and the residue was sublimated at 2.5 Pa/100° C. to obtain 8.80 g (yield: 34.2%) of a white solid.

$^1$H-NMR (Benzene-d$_6$, δ ppm) 4.79 (m, 4H, C$_5$H$_4$Et) 4.72 (t, J=2.5 Hz, 4H, C$_5$H$_4$Et) 2.39 (q, J=7.3 Hz, 4H, CH$_3$CH$_2$Cp) 1.07 (t, J=7.3 Hz, 6H, CH$_3$CH$_2$Cp) −0.87 (t, J=10.5 Hz, 1H, Ta—H) −2.41 (d, J=10.5 Hz, 2H, Ta—H)

$^{13}$C-NMR (Benzene-d$_6$, δ ppm) 114.90 (C$_5$H$_4$Et) 85.66 (C$_5$H$_4$Et) 84.43 (C$_5$H$_4$Et) 23.78 (CH$_3$CH$_2$Cp) 15.96 (CH$_3$CH$_2$Cp)

EXAMPLE 5

Synthesis of bis(ethylcyclopentadienyl)hydridocarbonyl-tantalum (Ta(EtCp)$_2$(CO)H)

8.30 g (22.4 mmol) of bis(ethylcyclopentadienyl)tri-hydridotantalum was heated to 135° C. in nonane (150 ml) under a carbon monoxide atmosphere, and stirring for 4 hours. The solvent was distilled away from the reaction mixture. 500 ml of hexane was added to the residue, and insoluble contents were filtered out. When the filtrate was concentrated to about 100 ml, and then cooled to −70° C., a solid was formed. The supernatant was removed, and the solid was washed with 10 ml of hexane two times, and dried in vacuo to obtain a purple solid. When this solid was allowed to stand at room temperature, the solid was converted into a liquid. This liquid was distilled in vacuo to obtain 5.40 g (yield: 60.8%) of a purple liquid. Thermal analysis result of the tantalum compound obtained is shown in FIG. 2. It is seen from this Figure that the tantalum compound obtained has a wide temperature range at which the compound can vaporize stably without decomposition, and thermally decomposes in the vicinity of 240° C., and the compound is therefore suitable as a raw material of a tantalum-containing thin film by CVD method or ALD method.

$^1$H-NMR (Benzene-d$_6$, δ ppm) 4.53 (m, 2H, C$_5$H$_4$Et) 4.46 (m, 2H, C$_5$H$_4$Et) 4.42 (m, 2H, C$_5$H$_4$Et) 4.35 (m, 2H, C$_5$H$_4$Et) 2.26 (m, 4H, CH$_3$CH$_2$ Cp) 1.00 (t, J=7.5 Hz, 6H, CH$_3$CH$_2$Cp) −6.16 (s, 1H, Ta—H)

$^{13}$C-NMR (Benzene-d$_6$, δ ppm) 264.26 (CO) 112.38 (C$_5$H$_4$Et) 83.71 (C$_5$H$_4$Et) 83.40 (C$_5$H$_4$Et) 82.08 (C$_5$H$_4$Et) 79.61 (C$_5$H$_4$Et) 23.26 (CH$_3$CH$_2$ Cp) 15.92 (CH$_3$CH$_2$ Cp)

IR (Nujol, ν cm$^{-1}$) 1896 (CO) 1721 (Ta—H)

Compositional Analysis

Ta content (ICP emission analysis)
    46.4 wt % (theoretical value 45.7 wt %)

CH content (Elemental analysis)
C 46.2 wt % (theoretical value 45.5 wt %)
H 5.1 wt % (theoretical value 4.8 wt %)

MS (GC/MS, EI)
Molecular ion peak of bis(ethylcyclopentadienyl)-hydridocarbonyltantalum by $^{181}$Ta, m/z: 396
Chart of this mass spectrum is shown in FIG. 4.

EXAMPLE 6

Formation of Tantalum-Containing Thin Film by CVD Method Using hydridobis(propylcyclopentadienyl)carbonyltantalum as Raw Material A cylinder containing hydridobis(propylcyclopentadienyl)carbonyltantalum therein was heated to 100° C., inner pressure was maintained at 100 Torr, and an argon gas as a carrier gas was blown at a flow rate of 100 sccm to vaporize the compound. This was diluted with an argon gas at a flow rate of 100 sccm, and introduced into a reaction chamber maintained at 4 Torr. This gas was thermally decomposed on a silicon oxide/silicon substrate heated to 400° C. to deposit a thin film thereon. As a result of analyzing a 100 nm deposited thin film with X-ray photoelectron spectroscopy analyzer (XPS), it was found to be a tantalum-containing thin film free of nitrogen.

EXAMPLE 7

Formation of Tantalum-Containing Thin Film by CVD Method Using hydridobis(propylcyclopentadienyl)carbonyltantalum as Raw Material and Adding Ammonia A cylinder containing hydridobis(propylcyclopentadienyl)carbonyltantalum therein was heated to 100° C., inner pressure was maintained at 100 Torr, and an argon gas as a carrier gas was blown at a flow rate of 100 sccm to vaporize the compound. This was diluted with an argon gas at a flow rate of 100 sccm, and introduced into a reaction chamber maintained at 4 Torr, and at the same time, an ammonia gas was introduced into the reaction chamber at a flow rate of 2 sccm. This gas was thermally decomposed on a silicon oxide/silicon substrate heated to 400° C. to deposit a thin film thereon. As a result of analyzing a 100 nm deposited thin film with X-ray photoelectron spectroscopy analyzer (XPS), it was found to be a tantalum-containing thin film containing nitrogen.

EXAMPLE 8

Formation of Tantalum-Containing Thin Film on Silicon Oxide/Silicon Substrate by Thermal CVD Method Using bis(ethylcyclopentadienyl)hydridocarbonyltantalum as Raw Material A cylinder containing bis(ethylcyclopentadienyl)-hydridocarbonyltantalum therein was heated to 90° C., inner pressure was maintained at 100 Torr, and an argon gas as a carrier gas was blown at a flow rate of 100 sccm to vaporize the compound. This was diluted with an argon gas at a flow rate of 100 sccm, and introduced into a reaction chamber maintained at 10 Torr. This gas was thermally decomposed on a silicon oxide/silicon substrate heated to 600° C. to deposit a thin film thereon. As a result of analyzing a 175 nm deposited thin film with X-ray photoelectron spectroscopy analyzer (XPS), it was found to be a thin film having a composition of carbon 72%, oxygen 18% and tantalum 10%. A distribution state of elements in a depth direction measured by Auger electron spectroscopy analyzer (AES) is shown in FIG. 5. Further, resistivity was measured with a 4-pin resistivity meter, and it was found to be $1.24 \times 10^5$ μΩ·cm.

EXAMPLE 9

Formation of Tantalum-Containing Thin Film on Silicon Oxide/Silicon Substrate by ECR Plasma CVD Method Using bis(ethylcyclopentadienyl)hydridocarbonyltantalum as Raw Material A cylinder containing bis(ethylcyclopentadienyl)-hydridocarbonyltantalum therein was heated to 90° C., inner pressure was maintained at 50 Torr, and an argon gas as a carrier gas was blown at a flow rate of 28 sccm to vaporize the compound. This was introduced into a plasma-generating reaction chamber maintained at $1.5 \times 10^{-3}$ Torr to deposit a thin film on a silicon oxide/silicon substrate heated to 300° C. Plasma was generated by 2.45 GHz, 600 W microwave and 875 G applied magnetic field in an argon gas at a flow rate of 10 sccm. As a result of analyzing a 10 nm deposited thin film with X-ray photoelectron spectroscopy analyzer (XPS), it was found to be a thin film having a composition of carbon 26%, oxygen 15%, tantalum 56% and nitrogen 3%. A distribution state of elements in a depth direction measured by Auger electron spectroscopy analyzer (AES) is shown in FIG. 6. Further, resistivity was measured with a 4-pin resistivity meter, and it was found to be 80 μΩ·cm.

EXAMPLE 10

Formation of Tantalum-Containing Thin Film on Silicon Substrate by ECR Plasma CVD Method Using bis(ethylcyclopentadienyl)hydridocarbonyltantalum as Raw Material A cylinder containing bis(ethylcyclopentadienyl)-hydridocarbonyltantalum therein was heated to 90° C., inner pressure was maintained at 50 Torr, and an argon gas as a carrier gas was blown at a flow rate of 28 sccm to vaporize the compound. This was introduced into a plasma-generating reaction chamber maintained at $1.5 \times 10^{-3}$ Torr to deposit a thin film on a silicon substrate heated to 400° C. Plasma was generated by 2.45 GHz, 600 W microwave and 875 G applied magnetic field in an argon gas at a flow rate of 10 sccm. As a result of analyzing a 5 nm deposited thin film with X-ray photoelectron spectroscopy analyzer (XPS), it was found to be a thin film having a composition of carbon 26%, oxygen 19%, tantalum 51% and nitrogen 4%. Further, resistivity was measured with a 4-pin resistivity meter, and it was found to be 100 μΩ·cm.

EXAMPLE 11

Formation of Tantalum-Containing Thin Film on Silicon Substrate by Hydrogenation ECR Plasma CVD Method Using bis(ethylcyclopentadienyl)hydridocarbonyltantalum as Raw Material A cylinder containing bis(ethylcyclopentadienyl)-hydridocarbonyltantalum therein was heated to 90° C., inner pressure was maintained at 70 Torr, and an argon gas as a carrier gas was blown at a flow rate of 55 sccm to vaporize the compound. This was introduced into a plasma-generating reaction chamber maintained at $7.5 \times 10^{-3}$ Torr to deposit a thin film on a silicon substrate heated to 300° C. Plasma was generated by 2.45 GHz, 600 W microwave and 875 G applied magnetic field in an argon gas containing 4% hydrogen at a flow rate of 40 sccm. As a result of analyzing a 10 nm deposited thin film with X-ray photoelectron spectroscopy analyzer (XPS), it was found to be a thin film having a composition of carbon 31%, oxygen 13% and tantalum 56%. Further, resistivity was measured with a 4-pin resistivity meter, and it was found to be 76 μΩ·cm.

While the invention has been described in detail and with reference to specific embodiments thereof, it will be apparent to one skilled in the art that various changes and modifications can be made therein without departing from the spirit and scope thereof.

This application is based on Japanese patent application (Patent Application No. 2005-26727) filed Feb. 2, 2005, Japanese patent application (Patent Application No. 2005-26728) filed Feb. 2, 2005, Japanese patent application (Patent Application No. 2005-243053) filed Aug. 24, 2005, Japanese patent application (Patent Application No. 2005-243054) filed Aug. 24, 2005, and Japanese patent application (Patent Application No. 2005-351086) filed Dec. 5, 2005, the contents thereof being incorporated herein by reference.

INDUSTRIAL APPLICABILITY

By the present invention, a novel tantalum compound which enables to selectively form a tantalum-containing thin film free of halogen and the like, and various tantalum-containing thin films which contain the desired element, and a method for producing the same can be provided. Further, a method for stably forming a tantalum-containing thin film which contains the desired element can be provided.

The invention claimed is:

1. A tantalum compound represented by the following general formula (1)

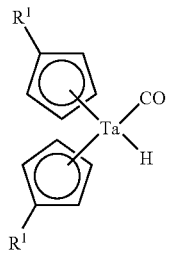

(1)

in which $R^1$ represents a straight-chain alkyl group having from 2 to 6 carbon atoms.

2. The tantalum compound as claimed in claim 1, wherein $R^1$ is a straight-chain alkyl group having from 2 to 4 carbon atoms.

3. The tantalum compound as claimed in claim 2, wherein $R^1$ is an ethyl group or a propyl group.

4. The tantalum compound as claimed claim 3, wherein $R^1$ is an ethyl group.

5. A method for producing a tantalum compound represented by the following general formula (1)

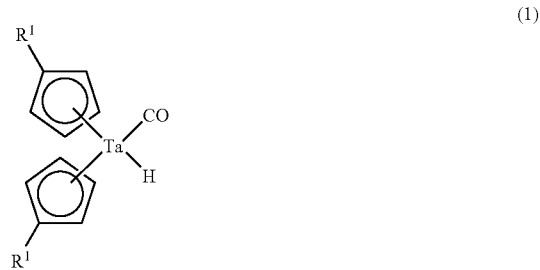

(1)

in which $R^1$ represents a straight-chain alkyl group having from 2 to 6 carbon atoms, which comprises reacting carbon monoxide with a tantalum compound represented by the general formula (2)

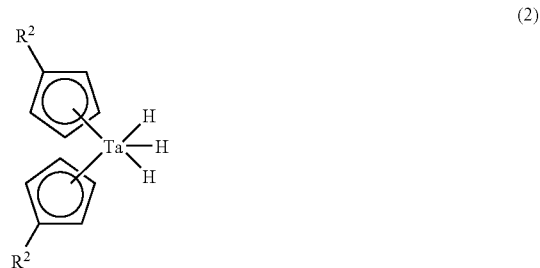

(2)

in which $R^2$ represents a straight-chain alkyl group having from 2 to 6 carbon atoms.

6. A method for forming a tantalum-containing thin film, which comprises using a tantalum compound represented by the following general formula (6) as a raw material

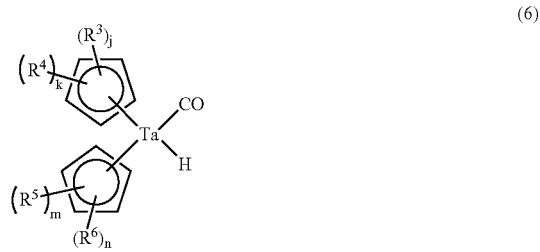

(6)

in which j, k, m and n is an integer of from 1 to 4 satisfying j+k=5 and m+n=5, and $R^3$ to $R^6$ represent a hydrogen atom, an alkyl group having from 1 to 6 carbon atoms, a trialkylsilyl group having from 3 to 6 carbon atoms or an alkyl group having from 1 to 6 carbon atoms which may be substituted with at least one fluorine atom.

7. The method for forming a tantalum-containing thin film as claimed in claim 6, wherein j=1, m=1, $R^3$ and $R^5$ are a straight-chain alkyl group having from 2 to 4 carbon atoms, and $R^4$ and $R^6$ are a hydrogen atom.

8. The method for forming a tantalum-containing thin film as claimed in claim 7, wherein j=1, m=1, $R^3$ and $R^5$ are an ethyl group or a propyl group, and $R^4$ and $R^6$ are a hydrogen atom.

9. The method for forming a tantalum-containing thin film as claimed in any one of claims 8, wherein j=1, m=1, $R^3$ and $R^5$ are an ethyl group, and $R^4$ and $R^6$ are a hydrogen atom.

* * * * *